United States Patent
Zellner et al.

US011568987B2

(10) Patent No.: US 11,568,987 B2
(45) Date of Patent: Jan. 31, 2023

(54) FACILITATION OF CONDITIONAL DO NOT RESUSCITATE ORDERS

(71) Applicant: AT&T Intellectual Property I, L.P., Atlanta, GA (US)

(72) Inventors: Brittaney Zellner, Smyrna, GA (US); Sameena Khan, Peachtree Corners, GA (US); Ryan Schaub, Berkeley Lake, GA (US); Barrett Kreiner, Woodstock, GA (US); Ari Craine, Marietta, GA (US); Robert Koch, Peachtree Corners, GA (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 244 days.

(21) Appl. No.: 16/851,503

(22) Filed: Apr. 17, 2020

(65) Prior Publication Data

US 2021/0327573 A1    Oct. 21, 2021

(51) Int. Cl.
*G16H 40/67* (2018.01)
*A61N 1/39* (2006.01)
(Continued)

(52) U.S. Cl.
CPC ........... *G16H 40/67* (2018.01); *A61H 31/007* (2013.01); *A61N 1/3904* (2017.08);
(Continued)

(58) Field of Classification Search
CPC ........ G06H 40/67; G06H 40/20; G16H 10/60; A61N 1/3904; G06Q 10/109; G06Q 50/265; H04W 4/023; H04W 4/20
(Continued)

(56) References Cited

U.S. PATENT DOCUMENTS 3,041,636 A1    10/2011  Hunter et al.
8,874,592 B2    10/2014  Flake et al.
(Continued)

FOREIGN PATENT DOCUMENTS

CA    2739793 A1 *   4/2010    ........... G06F 19/345
CA    3047016 A1     6/2018
(Continued)

OTHER PUBLICATIONS

Steiner et al., Moral Distress at the End of a Life, Feb. 2, 2018, Journal of Pain and Symptom Management, vol. 55, 5 pages (Year: 2018).*
(Continued)

*Primary Examiner* — Mong-Thuy T Tran
(74) *Attorney, Agent, or Firm* — Amin, Turocy & Watson, LLP

(57) ABSTRACT

This disclosure describes a solution to enable more useful and responsive methods for a person's wishes for resuscitation actions to be canceled or discontinued in the event of a medical event. In this solution, a person can record their do not resuscitate (DNR) wishes with more specificity. For instance, they can specify conditions for treatment or non-treatment in the event of a medical emergency that would otherwise call for live-saving procedures or the use of an automated external defibrillator (AED) device. Conditional DNR data can be recorded in an electronic device (e.g., emergency pendant or smart watch, or in an electronic device) implanted within or on the person's body. This data can also be stored in a database accessible via a network.

20 Claims, 10 Drawing Sheets

(51) Int. Cl.

| | | |
|---|---|---|
| *G16H 10/60* | (2018.01) | |
| *G06Q 50/26* | (2012.01) | |
| *G16H 40/20* | (2018.01) | |
| *A61H 31/00* | (2006.01) | |
| *H04W 4/20* | (2018.01) | |
| *H04W 4/02* | (2018.01) | |
| *G06Q 10/10* | (2012.01) | |

(52) U.S. Cl.
CPC ......... *G06Q 10/109* (2013.01); *G06Q 50/265* (2013.01); *G16H 10/60* (2018.01); *G16H 40/20* (2018.01); *H04W 4/023* (2013.01); *H04W 4/20* (2013.01); *A61H 2201/501* (2013.01)

(58) Field of Classification Search
USPC ........................................................ 455/404
See application file for complete search history.

(56) References Cited

U.S. PATENT DOCUMENTS

| | | | |
|---|---|---|---|
| 8,963,806 | B1 | 2/2015 | Starner et al. |
| 9,916,693 | B1 | 3/2018 | Carr et al. |
| 9,928,657 | B2 | 3/2018 | De Pasquale |
| 10,043,211 | B2 | 8/2018 | Joshi et al. |
| 10,129,508 | B1 | 11/2018 | Hillman et al. |
| 10,262,019 | B1 | 4/2019 | Reiner et al. |
| 10,891,792 | B1 | 1/2021 | Bhushan et al. |
| 11,055,390 | B1 * | 7/2021 | Kragh ................... G16H 10/60 |
| 11,055,797 | B1 | 7/2021 | Carone |
| 11,172,035 | B2 * | 11/2021 | Reineke ................. H04L 67/52 |
| 11,182,224 | B2 * | 11/2021 | George .................. G06F 16/27 |
| 11,238,406 | B1 | 2/2022 | Zhuo et al. |
| 11,334,725 | B2 * | 5/2022 | Hewitt ................... G06F 40/35 |
| 2002/0199156 | A1 | 12/2002 | Chess et al. |
| 2004/0258314 | A1 | 12/2004 | Hashimoto |
| 2008/0052201 | A1 | 2/2008 | Bodin et al. |
| 2008/0086508 | A1 | 4/2008 | Ballew |
| 2008/0310707 | A1 | 12/2008 | Kansal et al. |
| 2009/0095813 | A1 | 4/2009 | Chang et al. |
| 2009/0259579 | A1 | 10/2009 | Hanebeck |
| 2010/0042531 | A1 | 2/2010 | Heaton et al. |
| 2012/0008838 | A1 | 1/2012 | Guyon et al. |
| 2012/0320033 | A1 | 12/2012 | Papaefstathiou et al. |
| 2013/0024327 | A1 | 1/2013 | Nargizian |
| 2014/0164305 | A1 | 6/2014 | Lynch et al. |
| 2014/0232519 | A1 | 8/2014 | Allen et al. |
| 2014/0343961 | A1 * | 11/2014 | Thesman ............... G16H 50/20 705/2 |
| 2014/0348365 | A1 | 11/2014 | Edwards |
| 2015/0012467 | A1 | 1/2015 | Greystoke et al. |
| 2015/0036856 | A1 | 2/2015 | Pruthi et al. |
| 2015/0113422 | A1 * | 4/2015 | Pfeiffer ................. G16H 40/63 715/739 |
| 2015/0199754 | A1 | 7/2015 | Greystoke et al. |
| 2016/0117646 | A1 | 4/2016 | Lerick et al. |
| 2016/0163186 | A1 | 6/2016 | Davidson et al. |
| 2016/0224734 | A1 * | 8/2016 | Ryan ...................... G16Z 99/00 |
| 2017/0103440 | A1 | 4/2017 | Xing et al. |
| 2017/0287038 | A1 | 10/2017 | Krasadakis |
| 2017/0308802 | A1 | 10/2017 | Ramsoy et al. |
| 2018/0159838 | A1 | 6/2018 | Dintenfass |
| 2018/0173323 | A1 | 6/2018 | Harvey et al. |
| 2018/0239144 | A1 | 8/2018 | Woods et al. |
| 2018/0309806 | A1 | 10/2018 | Huynh et al. |
| 2019/0108603 | A1 | 4/2019 | Waslander et al. |
| 2019/0216452 | A1 | 7/2019 | Nawana et al. |
| 2019/0236732 | A1 | 8/2019 | Speasl et al. |
| 2019/0244267 | A1 | 8/2019 | Rattner et al. |
| 2019/0302460 | A1 | 10/2019 | Kaul et al. |
| 2019/0318818 | A1 * | 10/2019 | Chaudhuri ............. A61M 1/28 |
| 2019/0341050 | A1 | 11/2019 | Diamant et al. |
| 2020/0085380 | A1 * | 3/2020 | Sampson ........... A61B 5/14551 |
| 2020/0134753 | A1 | 4/2020 | Vickers |
| 2020/0143270 | A1 | 5/2020 | Yang et al. |
| 2020/0335219 | A1 * | 10/2020 | Fogel ..................... G16H 50/30 |
| 2021/0103452 | A1 | 4/2021 | Pratt et al. |
| 2021/0216647 | A1 | 7/2021 | Sarhaddar et al. |

FOREIGN PATENT DOCUMENTS

| | | | | |
|---|---|---|---|---|
| EP | 2266662 | B1 * | 8/2016 | ........... A61H 31/005 |
| WO | 2016/069746 | A1 | 5/2016 | |

OTHER PUBLICATIONS

Cristina et al., Do not resuscitate order: a view throughout the world, 2013, Journal of Critical Care, Elsevier, 16 pages (Year: 2013).*

Mehter et al., "Do not resuscitate" Decisions in Acute Respiratory Distress Syndrome, 2014, AnnalsATS, vol. 11, 5pages (Year: 2014).*

Non Final Office Action received for U.S. Appl. No. 16/851,541 dated Sep. 23, 2021, 43 pages.

Non Final Office Action received for U.S. Appl. No. 16/850,656 dated Dec. 17, 2021, 144 pages.

Clauser, Grant "These Devices Can Prevent Major Home Damage and Save Your Money", The New York Times, Feb. 17, 2020, URL: https://www.nytimes.com/2020/02/17/smarter-living/wirecutter/5-small-smart-devices-that-can-prevent-major-home-damage.html, 2020, 3 pages.

Office Action dated Feb. 22, 2022 for U.S. Appl. No. 16/850,679, 49 pages.

Patki, Effect of 6% hydroxyethyl starch-450 and low molecular weight dextran on blood sugar levels during surgery under subarachnoid block: A prospective randomised study, Indian J Anaesth, Sep. 2010;54(5):448-52 (Year: 2010).

Navin, Real-time skin analysis filters (Order No. 1603812). Available from ProQuest Dissertations and Theses Professional. ( 1734473922). Retrieved from https://dialog.proquest.com/professional/docview/1734473922?accountid=131444 (Year: 2014).

Mavin, Skin lens: Skin assessment video filters, 2014 IEEE International Conference on Systems, Man, and Cybernetics (SMC), 2014, pp. 1033-1038, doi: 10.1109/SMC.2014.6974049. (Year: 2014).

Non Final Office action received for U.S. Appl. No. 16/851,514 dated Jan. 29, 2021, 40 pages.

Zhang et al, "Time-Series Prediction of Environmental Noise for Urban IoT Based on Long Short-Term Memory Recurrent Neural Network." pp. 1-18. (Year: 2020).

Office Action dated Apr. 1, 2021 for U.S. Appl. No. 16/850,632, 42 pages.

Stipetic, et al. "7 Best Real Estate and Architecture Augmented Reality Apps." https://www.supersuperagency.com/blog/7-best-real-estate-architecture-augmented-reality-apps. Last Accessed Mar. 31, 2020. 10 pages.

Goldsmith, et al. "Augmented Reality Environmental Monitoring Using Wireless Sensor Networks." Proceedings of the 2008 12th International Conference on Information Visualisation (IV08), 2008. 7 pages.

Fukuda, et al. "An indoor thermal environment design system for renovation using augmented reality." Journal of Computational Design and Engineering 6 (2019) 179-188. 10 pages.

Natephra, et al. "Live data visualization of IoT sensors using Augmented Reality (AR) and BIM." 36th International Symposium on Automation and Robotics in Construction (ISARC 2019). 8 pages.

Final Office Action received for U.S. Appl. No. 16/850,656 dated Mar. 22, 2022, 81 pages.

Non Final Office Action received for U.S. Appl. No. 16/851,471 dated May 31, 2022, 53 pages.

Final Office Action received for U.S. Appl. No. 16/850,679 dated Jun. 24, 2022, 57 pages.

Gao et al., "EarEcho: Using Ear Canal Echo for Wearable Authentication", Proceedings of the ACM on Interactive, Mobile, Wearable and Ubiquitous Technologies, vol. 3, No. 3, Article 81, Sep. 2019, p. 81.1-81.24.

Schneegass et al., "SkullConduct: Biometric user Identification on Eyewear Computers using Bone Conduction Through the Skull",

(56) References Cited

OTHER PUBLICATIONS

CHI '16: Proceedings of the 2016 CHI Conference on Human Factors in Computing Systems, 2016, pp. 1379-1384.
Notice of Allowance received for U.S. Appl. No. 16/850,656 dated Aug. 11, 2022, 62 pages.
Anonymous "Virtual Doormen on the go in New Mobile App", Real Estate Weekly, vol. 57, No. 32, May 23, 2012, 2 pages.
Brassfield, Mike "This Argumentative New Chat Bot Haggles with Comcast so you don't have to", downloaded from <https://www.thepennyhoarder.com/save-money/how-trim-can-negotiate-your-comcast-bill/>, 2020, retrieved on Jun. 28, 2022, 5 pages.
Lewis et al., "Deal or No Deal? Training AI Bots to Negotiate", Ai Research, MI Applications, downloaded from <https://engineering.fb.com/2017/06/14/ml-applications/deal-or-no-deal-training-ai-bots-to-negotiate/>, Jun. 14, 2017, 5 pages.
Dinah, Brin, "Recruiting Bots are here to Stay: More companies use 'Bots' to Aid the Hiring Process", HRNews, Dec. 16, 2016, 3 pages.
McGloin, Cathal "Beyond the Virtual Assistant: Putting Bots to Work in Customer Service", The Wayback Machine, downloaded from <https://web.archive.org/web/20190307220605/https://servisbot.com/beyond-the-virtual-assistant/>, Mar. 7, 2019, 4 pages.

\* cited by examiner

FACILITATION OF CONDITIONAL DO NOT RESUSCITATE ORDERS

TECHNICAL FIELD

This disclosure relates generally to facilitating do not resuscitate orders. For example, this disclosure relates to facilitating do not resuscitate orders based on conditional logic.

BACKGROUND

Do not resuscitate (DNR), also known as no code or allow natural death, is a legal order, written or oral depending on country, indicating that a person does not want to receive cardiopulmonary resuscitation (CPR) if that person's heart stops beating. Sometimes it also prevents other medical interventions. The legal status and processes surrounding DNR orders vary from country to country. Most commonly, the order is placed by a physician based on a combination of medical judgement and patient wishes and values The above-described background relating to a facilitation of conditional do not resuscitate orders is merely intended to provide a contextual overview of some current issues, and is not intended to be exhaustive. Other contextual information may become further apparent upon review of the following detailed description.

BRIEF DESCRIPTION OF THE DRAWINGS

Non-limiting and non-exhaustive embodiments of the subject disclosure are described with reference to the following figures, wherein like reference numerals refer to like parts throughout the various views unless otherwise specified.

DETAILED DESCRIPTION

Figure 1:
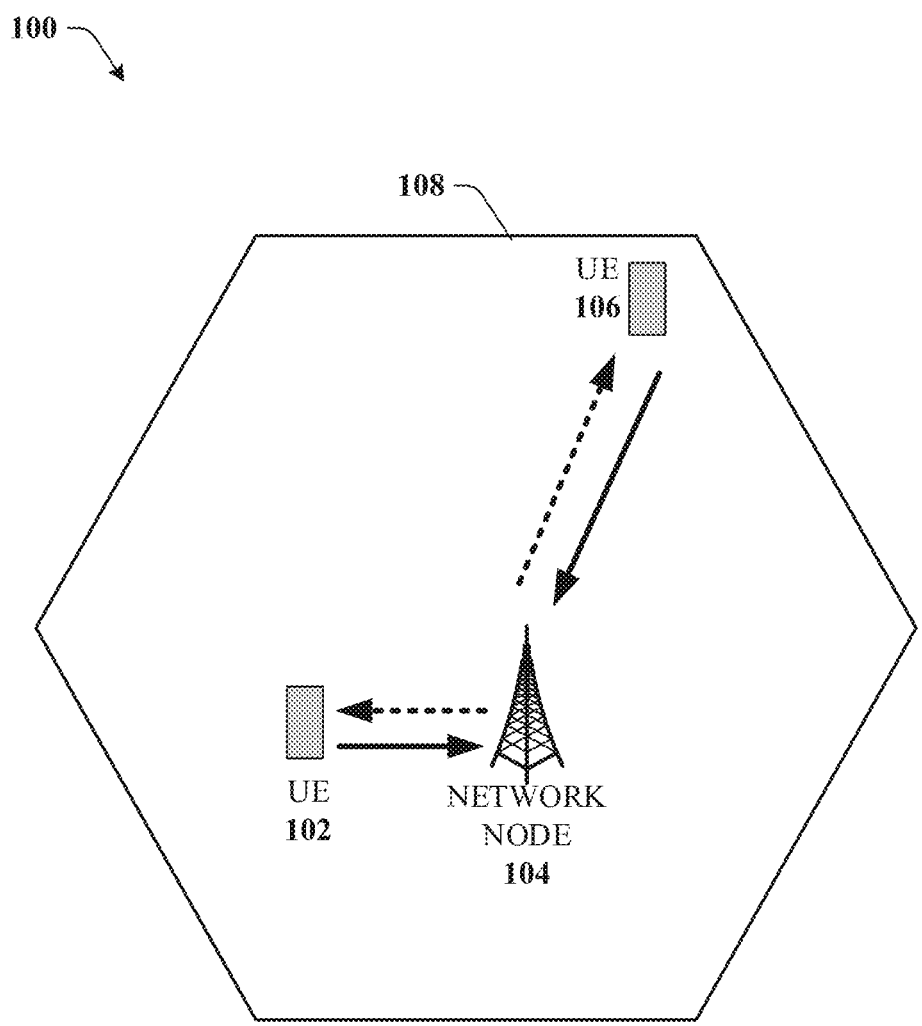
FIG. 1 illustrates an example wireless communication system in which a network node device (e.g., network node) and user equipment (UE) can implement various aspects and embodiments of the subject disclosure.

In the following description, numerous specific details are set forth to provide a thorough understanding of various embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment," or "an embodiment," means that a particular feature, structure, or characteristic described in connection with the embodiment is included in at least one embodiment. Thus, the appearances of the phrase "in one embodiment," "in one aspect," or "in an embodiment," in various places throughout this specification are not necessarily all referring to the same embodiment. Furthermore, the particular features, structures, or characteristics may be combined in any suitable manner in one or more embodiments.

As utilized herein, terms "component," "system," "interface," and the like are intended to refer to a computer-related entity, hardware, software (e.g., in execution), and/or firmware. For example, a component can be a processor, a process running on a processor, an object, an executable, a program, a storage device, and/or a computer. By way of illustration, an application running on a server and the server can be a component. One or more components can reside within a process, and a component can be localized on one computer and/or distributed between two or more computers.

Further, these components can execute from various machine-readable media having various data structures stored thereon. The components can communicate via local and/or remote processes such as in accordance with a signal having one or more data packets (e.g., data from one component interacting with another component in a local system, distributed system, and/or across a network, e.g., the Internet, a local area network, a wide area network, etc. with other systems via the signal).

As another example, a component can be an apparatus with specific functionality provided by mechanical parts operated by electric or electronic circuitry; the electric or electronic circuitry can be operated by a software application or a firmware application executed by one or more processors; the one or more processors can be internal or external to the apparatus and can execute at least a part of the software or firmware application. As yet another example, a component can be an apparatus that provides specific functionality through electronic components without mechanical parts; the electronic components can include one or more processors therein to execute software and/or firmware that confer(s), at least in part, the functionality of the electronic components. In an aspect, a component can emulate an electronic component via a virtual machine, e.g., within a cloud computing system.

The words "exemplary" and/or "demonstrative" are used herein to mean serving as an example, instance, or illustration. For the avoidance of doubt, the subject matter disclosed herein is not limited by such examples. In addition, any aspect or design described herein as "exemplary" and/or "demonstrative" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, such terms are intended to be inclusive—in a manner similar to the term "comprising" as an open transition word - without precluding any additional or other elements.

As used herein, the term "infer" or "inference" refers generally to the process of reasoning about, or inferring states of, the system, environment, user, and/or intent from a set of observations as captured via events and/or data. Captured data and events can include user data, device data, environment data, data from sensors, sensor data, application data, implicit data, explicit data, etc. Inference can be employed to identify a specific context or action, or can generate a probability distribution over states of interest based on a consideration of data and events, for example.

Inference can also refer to techniques employed for composing higher-level events from a set of events and/or data. Such inference results in the construction of new events or actions from a set of observed events and/or stored event data, whether the events are correlated in close temporal proximity, and whether the events and data come from one or several event and data sources. Various classification schemes and/or systems (e.g., support vector machines, neural networks, expert systems, Bayesian belief networks, fuzzy logic, and data fusion engines) can be employed in connection with performing automatic and/or inferred action in connection with the disclosed subject matter.

In addition, the disclosed subject matter can be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, machine-readable device, computer-readable carrier, computer-readable media, or machine-readable media. For example, computer-readable media can include, but are not limited to, a magnetic storage device, e.g., hard disk; floppy disk; magnetic strip(s); an optical disk (e.g., compact disk (CD), a digital video disc (DVD), a Blu-ray Disc™ (BD)); a smart card; a flash memory device (e.g., card, stick, key drive); and/or a virtual device that emulates a storage device and/or any of the above computer-readable media.

As an overview, various embodiments are described herein to facilitate do not resuscitate orders. For simplicity of explanation, the methods (or algorithms) are depicted and described as a series of acts. It is to be understood and appreciated that the various embodiments are not limited by the acts illustrated and/or by the order of acts. For example, acts can occur in various orders and/or concurrently, and with other acts not presented or described herein. Furthermore, not all illustrated acts may be required to implement the methods. In addition, the methods could alternatively be represented as a series of interrelated states via a state diagram or events. Additionally, the methods described hereafter are capable of being stored on an article of manufacture (e.g., a machine-readable storage medium) to facilitate transporting and transferring such methodologies to computers. The term article of manufacture, as used herein, is intended to encompass a computer program accessible from any computer-readable device, carrier, or media, including a non-transitory machine-readable storage medium.

It should be noted that although various aspects and embodiments have been described herein in the context of 5G, Universal Mobile Telecommunications System (UMTS), and/or Long Term Evolution (LTE), or other next generation networks, the disclosed aspects are not limited to 5G, a UMTS implementation, and/or an LTE implementation as the techniques can also be applied in 3G, 4G or LTE systems. For example, aspects or features of the disclosed embodiments can be exploited in substantially any wireless communication technology. Such wireless communication technologies can include UMTS, Code Division Multiple Access (CDMA), Wi-Fi, Worldwide Interoperability for Microwave Access (WiMAX), General Packet Radio Service (GPRS), Enhanced GPRS, Third Generation Partnership Project (3GPP), LTE, Third Generation Partnership Project 2 (3GPP2) Ultra Mobile Broadband (UMB), High Speed Packet Access (HSPA), Evolved High Speed Packet Access (HSPA+), High-Speed Downlink Packet Access (HSDPA), High-Speed Uplink Packet Access (HSUPA), Zigbee, or another IEEE 802.12 technology. Additionally, substantially all aspects disclosed herein can be exploited in legacy telecommunication technologies.

Described herein are systems, methods, articles of manufacture, and other embodiments or implementations that can facilitate do not resuscitate orders. Facilitating do not resuscitate orders can be implemented in connection with any type of device with a connection to the communications network (e.g., a mobile handset, a computer, a handheld device, etc.) any Internet of things (JOT) device (e.g., toaster, coffee maker, blinds, music players, speakers, etc.), and/or any connected vehicles (cars, airplanes, space rockets, and/or other at least partially automated vehicles (e.g., drones)). In some embodiments the non-limiting term user equipment (UE) is used. It can refer to any type of wireless device that communicates with a radio network node in a cellular or mobile communication system. Examples of UE are target device, device to device (D2D) UE, machine type UE or UE capable of machine to machine (M2M) communication, PDA, Tablet, mobile terminals, smart phone, laptop embedded equipped (LEE), laptop mounted equipment (LME), USB dongles etc. Note that the terms element, elements and antenna ports can be interchangeably used but carry the same meaning in this disclosure. The embodiments are applicable to single carrier as well as to multicarrier (MC) or carrier aggregation (CA) operation of the UE. The term carrier aggregation (CA) is also called (e.g. interchangeably called) "multi-carrier system", "multi-cell operation", "multi-carrier operation", "multi-carrier" transmission and/or reception.

In some embodiments the non-limiting term radio network node or simply network node is used. It can refer to any type of network node that serves UE is connected to other network nodes or network elements or any radio node from where UE receives a signal. Examples of radio network nodes are Node B, base station (BS), multi-standard radio (MSR) node such as MSR BS, eNode B, network controller, radio network controller (RNC), base station controller (BSC), relay, donor node controlling relay, base transceiver station (BTS), access point (AP), transmission points, transmission nodes, RRU, RRH, nodes in distributed antenna system (DAS) etc.

Cloud radio access networks (RAN) can enable the implementation of concepts such as software-defined network (SDN) and network function virtualization (NFV) in 5G networks. Certain embodiments of this disclosure can comprise an SDN controller that can control routing of traffic within the network and between the network and traffic destinations. The SDN controller can be merged with the 5G network architecture to enable service deliveries via open application programming interfaces ("APIs") and move the network core towards an all internet protocol ("IP"), cloud based, and software driven telecommunications network. The SDN controller can work with, or take the place of policy and charging rules function ("PCRF") network elements so that policies such as quality of service and traffic management and routing can be synchronized and managed end to end.

This disclosure describes a solution to enable more useful and responsive methods for a person's wishes for resuscitation actions to be canceled or discontinued in the event of a medical event. Do not resuscitate (DNR) orders today are limited in many ways. A person can have only paper records of the order, which can or can not be immediately accessible. A person can wear a bracelet or other item that shows their DNR wishes. Other solutions exist, but do not offer interactivity and conditional DNR benefits. In this solution, a person can record their DNR wishes with more specificity, since they can specify conditions for treatment or no treatment in the event of a medical emergency that would otherwise call for live-saving procedures such as CPR or the use of an automated external defibrillator (AED) device. Conditional DNR data can be recorded in an electronic device (e.g., emergency pendant or smart watch, or in an electronic device) implanted within or on the person's body. This data can also be stored in a database accessible via a network.

The conditional DNR data can include data that represents the person's wishes and instructions for what conditions must exist for life-saving measures to be used or not. For instance, the person can wish that their DNR instructions be followed only if a probability that they will have permanent brain damage calculated to be at least 60%. Similarly, the person can want for resuscitation to be attempted only on certain days. For instance, they can want to try to avoid dying on the same day that their children and grandchildren have birthdays. Or they can not wish to die on Christmas day. These can be waiver dates for the DNR. The person can wish to die in a certain location (e.g., at home). They can specify location information (e.g., latitude/longitude coordinates or a range of coordinates) that represent an acceptable area for a DNR to be honored.

Additionally, the person can wish to ensure that specific other people are present, such as family members, for a DNR order to be effective. A device ID, such as an identifier for a family member's smartphone or other device can be stored. Similarly, the person can wish for resuscitation to be attempted, but only for a maximum period of time. Other conditional instructions can similarly be stored. These can include such data as the type of treatment to be provided and what is not to be provided. The specific type of treatment to provide can also use the conditional DNR data to determine whether or not to provide the stated type of treatment. For instance, the person can not wish to be intubated if the brain damage likelihood has reached 50%, and then invoke a complete DNR once it has reached 60%. When storing this data, the person can additionally sign, perhaps digitally, a power of attorney, thereby granting the conditional DNR power to communicate the instructions to a first responder or other party.

The communication of the DNR instructions can be accomplished in a number of ways depending on what communication means are available and who is available to receive the communication. The instructions can be delivered by a speaker on a device that is worn or carried by the person. This can be useful especially if a professional first responder is not present. The instructions to be presented can be determined by a DNR server that has access to the conditional DNR data and data describing the real-time conditions of the event. Likewise, a conditional DNR app on a device carried or worn by the person can determine the instructions to be presented. In either case, the instructions to be presented can be sent to a speech-to-text app and the results can be played over a speaker. In the case of a first responder, the instructions can be delivered to a communication device that they carry or wear. The first responder can proactively query using their device to determine if the person has conditional DNR on file. This can be necessary particularly if the person does not have their emergency pendant, smart watch, or other device with them.

The determination of what instructions to send can be made by the DNR server or the conditional DNR app. This determination can be based on comparing conditional DNR data for the person with data describing real-time conditions and using an algorithm to analyze the compared data and arrive at an instruction. For instance, the DNR server or conditional DNR app can compare the current date with any waiver dates in the conditional DNR data. If the current date is a waiver date, the instruction to be delivered can be: "attempt resuscitation". A similar process can be used with any conditional locations in the conditional DNR data. In order for this to take place, the person's device has location-aware capabilities that can be used by its conditional DNR app, or it can send its location to the DNR server.

In the case of persons required to be present in order for a DNR to be executed, the conditional DNR app on the person's device can attempt to locate other devices in the immediate area using a near-field communication, such as Bluetooth. In doing so, the user's CDNR app can successfully sense or pair with another device, such as a family member's smartphone. If the stored device ID is found, then the family member can be determined to be present and the instruction sent to be presented can be: "do not resuscitate". In the case of the person defining a maximum duration that they would want resuscitation to be attempted, the time when resuscitation attempts began can be noted in a number of ways, for instance, by the first responder speaking "beginning CPR", which can be captured and sent to the DNR server, with a timestamp. Or the first responder can say "CPR began at 9:02 PM", which can be sent to the DNR server, which can interpret the timestamp to use to be 9:02 PM.

In this case, the command sent by the DNR server or the CDNR app to the first responder can be "attempt resuscitation", which can be delivered periodically, until 9:22 PM, when the command sent can be "do not resuscitate". In the case of the person defining a threshold probability for permanent brain damage (below which they want resuscitation attempts and above which they do not), the first responder can speak "event began at 3:30 PM", which can be sent to the DNR server, which can record the beginning of the event to be at that time. Other environmental data, such as ambient air temperature, that can have an effect on the prospects for survival after resuscitation can also be sensed using sensors on the device of the first responder and can be sent to the DNR server.

The DNR server can use the data gathered to predict a real-time likelihood of survival with no brain damage. This can be done by an algorithm in a number of different ways. The DNR server can continually monitor the real-time percentage vs. the threshold and periodically deliver a command of "attempt resuscitation" until the threshold is reached, then it can send a "do not resuscitation" command.

The DNR command instructions can be delivered by the DNR server or the conditional DNR app to the AED device or other similar medical device. The AED can use its speakers to deliver the DNR instructions to a first responder or other user of the AED. Furthermore, the instructions delivered to the AED device can be used by it to disable the AED device from delivering treatment to the person if the instruction is "do not resuscitate".

In one embodiment, described herein is a method comprising receiving, by a server device comprising a processor, from a first mobile device, do not resuscitate data representative of a do not resuscitate order of a person. The method can comprise receiving, by the server device, status data representative of a status of the person. The method can comprise receiving, by the server device, indication data representative of an indication that a second mobile device is communicating with the first mobile device. Furthermore, in response to receiving the status data and the indication data, the method can comprise sending, by the server device via a wireless network, the do not resuscitate data to the second mobile device.

According to another embodiment, a system can facilitate receiving do not resuscitate data representative of a do not resuscitate order, associated with a person. The system can comprise receiving status data representative of a status of the person from a first mobile device. Additionally, the system can comprise receiving indication data, representative of an indication that a second mobile device is communicating with the first mobile device. Furthermore, in response to the receiving the status data and the receiving the indication data, the system can comprise sending the do not resuscitate data to the second mobile device.

According to yet another embodiment, described herein is a machine-readable medium that can perform the operations comprising receiving do not resuscitate data representative of a do not resuscitate command, associated with a living entity. The machine-readable medium operations can comprise receiving status data representative of a status of the living entity from a first mobile device. The machine-readable medium operations can comprise receiving indication data, representative of an indication that a second mobile device is in a proximity to the first mobile device. Additionally, in response to the receiving the status data and the receiving the indication data, the machine-readable medium operations can comprise receiving transmitting the do not resuscitate data to the second mobile device.

These and other embodiments or implementations are described in more detail below with reference to the drawings.

Referring now to FIG. 1, illustrated is an example wireless communication system 100 in accordance with various aspects and embodiments of the subject disclosure. In one or more embodiments, system 100 can comprise one or more user equipment UEs 102. The non-limiting term user equipment can refer to any type of device that can communicate with a network node in a cellular or mobile communication system. A UE can have one or more antenna panels having vertical and horizontal elements. Examples of a UE comprise a target device, device to device (D2D) UE, machine type UE or UE capable of machine to machine (M2M) communications, personal digital assistant (PDA), tablet, mobile terminals, smart phone, laptop mounted equipment (LME), universal serial bus (USB) dongles enabled for mobile communications, a computer having mobile capabilities, a mobile device such as cellular phone, a laptop having laptop embedded equipment (LEE, such as a mobile broadband adapter), a tablet computer having a mobile broadband adapter, a wearable device, a virtual reality (VR) device, a heads-up display (HUD) device, a smart car, a machine-type communication (MTC) device, and the like. User equipment UE 102 can also comprise IOT devices that communicate wirelessly.

In various embodiments, system 100 is or comprises a wireless communication network serviced by one or more wireless communication network providers. In example embodiments, a UE 102 can be communicatively coupled to the wireless communication network via a network node 104. The network node (e.g., network node device) can communicate with user equipment (UE), thus providing connectivity between the UE and the wider cellular network. The UE 102 can send transmission type recommendation data to the network node 104. The transmission type recommendation data can comprise a recommendation to transmit data via a closed loop MIMO mode and/or a rank-1 precoder mode.

A network node can have a cabinet and other protected enclosures, an antenna mast, and multiple antennas for performing various transmission operations (e.g., MIMO operations). Network nodes can serve several cells, also called sectors, depending on the configuration and type of antenna. In example embodiments, the UE 102 can send and/or receive communication data via a wireless link to the network node 104. The dashed arrow lines from the network node 104 to the UE 102 represent downlink (DL) communications and the solid arrow lines from the UE 102 to the network nodes 104 represents an uplink (UL) communication.

System 100 can further include one or more communication service provider networks 108 that facilitate providing wireless communication services to various UEs, including UE 102 and UE 106, via the network node 104 and/or various additional network devices (not shown) included in the one or more communication service provider networks 108. The one or more communication service provider networks 108 can include various types of disparate networks, including but not limited to: cellular networks, femto networks, picocell networks, microcell networks, internet protocol (IP) networks Wi-Fi service networks, broadband service network, enterprise networks, cloud based networks, and the like. For example, in at least one implementation, system 100 can be or include a large scale wireless communication network that spans various geographic areas. According to this implementation, the one or more communication service provider networks 108 can be or include the wireless communication network and/or various additional devices and components of the wireless communication network (e.g., additional network devices and cell, additional UEs, network server devices, etc.). The network node 104 can be connected to the one or more communication service provider networks 108 via one or more backhaul links. For example, the one or more backhaul links can comprise wired link components, such as a T1/E1 phone line, a digital subscriber line (DSL) (e.g., either synchronous or asynchronous), an asymmetric DSL (ADSL), an optical fiber backbone, a coaxial cable, and the like. The one or more backhaul links can also include wireless link components, such as but not limited to, line-of-sight (LOS) or non-LOS links which can include terrestrial air-interfaces or deep space links (e.g., satellite communication links for navigation).

Wireless communication system 100 can employ various cellular systems, technologies, and modulation modes to facilitate wireless radio communications between devices (e.g., the UE 102 and the network node 104). While example embodiments might be described for 5G new radio (NR) systems, the embodiments can be applicable to any radio access technology (RAT) or multi-RAT system where the UE operates using multiple carriers e.g. LTE FDD/TDD, GSM/GERAN, CDMA2000 etc.

For example, system 100 can operate in accordance with global system for mobile communications (GSM), universal mobile telecommunications service (UMTS), long term evolution (LTE), LTE frequency division duplexing (LTE FDD), LTE time division duplexing (TDD), high speed packet access (HSPA), code division multiple access (CDMA), wideband CDMA (WCMDA), CDMA2000, time division multiple access (TDMA), frequency division multiple access (FDMA), multi-carrier code division multiple access (MC-CDMA), single-carrier code division multiple access (SC-CDMA), single-carrier FDMA (SC-FDMA), orthogonal frequency division multiplexing (OFDM), discrete Fourier transform spread OFDM (DFT-spread OFDM) single carrier FDMA (SC-FDMA), Filter bank based multi-carrier (FBMC), zero tail DFT-spread-OFDM (ZT DFT-s-OFDM), generalized frequency division multiplexing (GFDM), fixed mobile convergence (FMC), universal fixed mobile convergence (UFMC), unique word OFDM (UW-OFDM), unique word DFT-spread OFDM (UW DFT-Spread-OFDM), cyclic prefix OFDM CP-OFDM, resource-block-filtered OFDM, Wi Fi, WLAN, WiMax, and the like. However, various features and functionalities of system 100 are particularly described wherein the devices (e.g., the UEs 102 and the network device 104) of system 100 are configured to communicate wireless signals using one or more multi carrier modulation schemes, wherein data symbols can be transmitted simultaneously over multiple frequency subcarriers (e.g., OFDM, CP-OFDM, DFT-spread OFMD, UFMC, FMBC, etc.). The embodiments are applicable to single carrier as well as to multicarrier (MC) or carrier aggregation (CA) operation of the UE. The term carrier aggregation (CA) is also called (e.g. interchangeably called) "multi-carrier system", "multi-cell operation", "multi-carrier operation", "multi-carrier" transmission and/or reception. Note that some embodiments are also applicable for Multi RAB (radio bearers) on some carriers (that is data plus speech is simultaneously scheduled).

In various embodiments, system 100 can be configured to provide and employ 5G wireless networking features and functionalities. 5G wireless communication networks are expected to fulfill the demand of exponentially increasing data traffic and to allow people and machines to enjoy gigabit data rates with virtually zero latency. Compared to 4G, 5G supports more diverse traffic scenarios. For example, in addition to the various types of data communication between conventional UEs (e.g., phones, smartphones, tablets, PCs, televisions, Internet enabled televisions, etc.) supported by 4G networks, 5G networks can be employed to support data communication between smart cars in association with driverless car environments, as well as machine type communications (MTCs). Considering the drastic different communication needs of these different traffic scenarios, the ability to dynamically configure waveform parameters based on traffic scenarios while retaining the benefits of multi carrier modulation schemes (e.g., OFDM and related schemes) can provide a significant contribution to the high speed/capacity and low latency demands of 5G networks. With waveforms that split the bandwidth into several sub-bands, different types of services can be accommodated in different sub-bands with the most suitable waveform and numerology, leading to an improved spectrum utilization for 5G networks.

To meet the demand for data centric applications, features of proposed 5G networks may comprise: increased peak bit rate (e.g., 20Gbps), larger data volume per unit area (e.g., high system spectral efficiency—for example about 3.5 times that of spectral efficiency of long term evolution (LTE) systems), high capacity that allows more device connectivity both concurrently and instantaneously, lower battery/power consumption (which reduces energy and consumption costs), better connectivity regardless of the geographic region in which a user is located, a larger numbers of devices, lower infrastructure development costs, and higher reliability of the communications. Thus, 5G networks may allow for: data rates of several tens of megabits per second should be supported for tens of thousands of users, 1 gigabit per second to be offered simultaneously to tens of workers on the same office floor, for example; several hundreds of thousands of simultaneous connections to be supported for massive sensor deployments; improved coverage, enhanced signaling efficiency; reduced latency compared to LTE.

The upcoming 5G access network may utilize higher frequencies (e.g., >6GHz) to aid in increasing capacity. Currently, much of the millimeter wave (mmWave) spectrum, the band of spectrum between 30 gigahertz (Ghz) and 300 Ghz is underutilized. The millimeter waves have shorter wavelengths that range from 10 millimeters to 1 millimeter, and these mmWave signals experience severe path loss, penetration loss, and fading. However, the shorter wavelength at mmWave frequencies also allows more antennas to be packed in the same physical dimension, which allows for large-scale spatial multiplexing and highly directional beamforming.

Performance can be improved if both the transmitter and the receiver are equipped with multiple antennas. Multi-antenna techniques can significantly increase the data rates and reliability of a wireless communication system. The use of multiple input multiple output (MIMO) techniques, which was introduced in the third-generation partnership project (3GPP) and has been in use (including with LTE), is a multi-antenna technique that can improve the spectral efficiency of transmissions, thereby significantly boosting the overall data carrying capacity of wireless systems. The use of multiple-input multiple-output (MIMO) techniques can improve mmWave communications, and has been widely recognized a potentially important component for access networks operating in higher frequencies. MIMO can be used for achieving diversity gain, spatial multiplexing gain and beamforming gain. For these reasons, MIMO systems are an important part of the 3rd and 4th generation wireless systems, and are planned for use in 5G systems.

Figure 2:
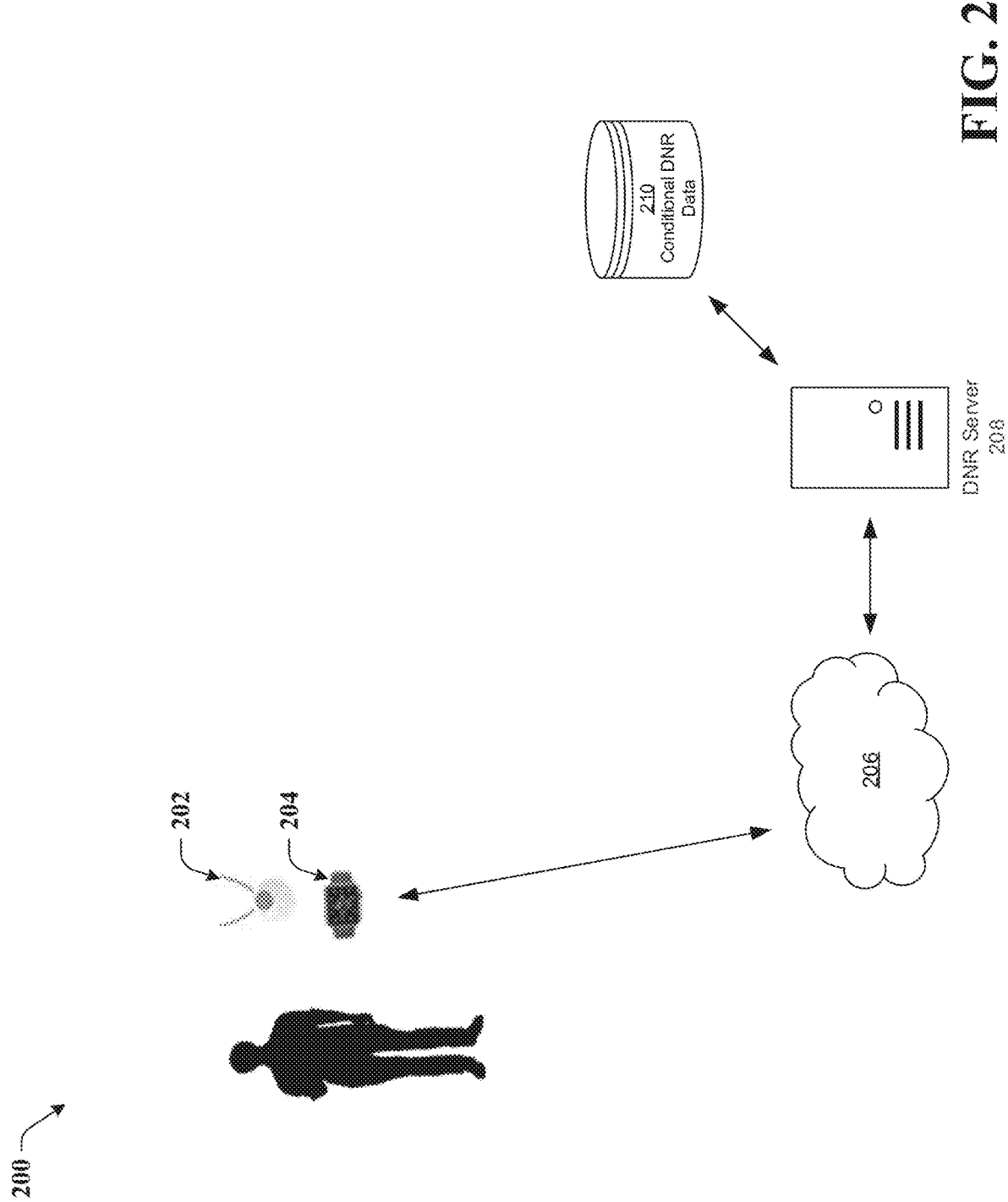
FIG. 2 illustrates an example schematic system block diagram of a DNR system according to one or more embodiments.

Referring now to FIG. 2, illustrated is an example schematic system block diagram of an example schematic system block diagram of a DNR system 200 according to one or more embodiments.

The communication of the DNR instructions can be accomplished in a number of ways depending on what communication means are available and who is available to receive the communication. The instructions can be delivered by a speaker on device 202 (depicted for illustrative purposes in FIG. 2 as a smart watch, bracelet, etc.), and/or a speaker on device 204 (depicted for illustrative purposes in FIG. 2 as a pendant, chain, etc.) that is worn or carried by the person. The instructions to be presented can be determined by a DNR server 208 (via a cloud-based network 206) that has access to the conditional DNR data (stored at a conditional DNR data repository 210) and data describing the real-time conditions of the event. Likewise, a conditional DNR app on the device 202 or device 204 carried or worn by the person can determine the instructions to be presented. In either case, the instructions to be presented can be sent to a speech-to-text app and the results can be played over a speaker.

The determination of what instructions to send can be made by the DNR server 208 or the conditional DNR app in response to a health event being determined to have occurred. This determination can be based on comparing conditional DNR data for the person with data describing real-time conditions and using an algorithm to analyze the compared data and arrive at an instruction at the DNR server 208. For instance, the DNR server 208 or conditional DNR app can compare the current date with any waiver dates in the conditional DNR data repository 210. If the current date is a waiver date, the instruction to be delivered to the device 202, 204 can be: "attempt resuscitation". A similar process can be used with any conditional locations in the conditional DNR data. In order for this to take place, the person's device 202, 204 has location-aware capabilities that can be used by its conditional DNR app, or it can send its location to the DNR server 208.

Figure 3:
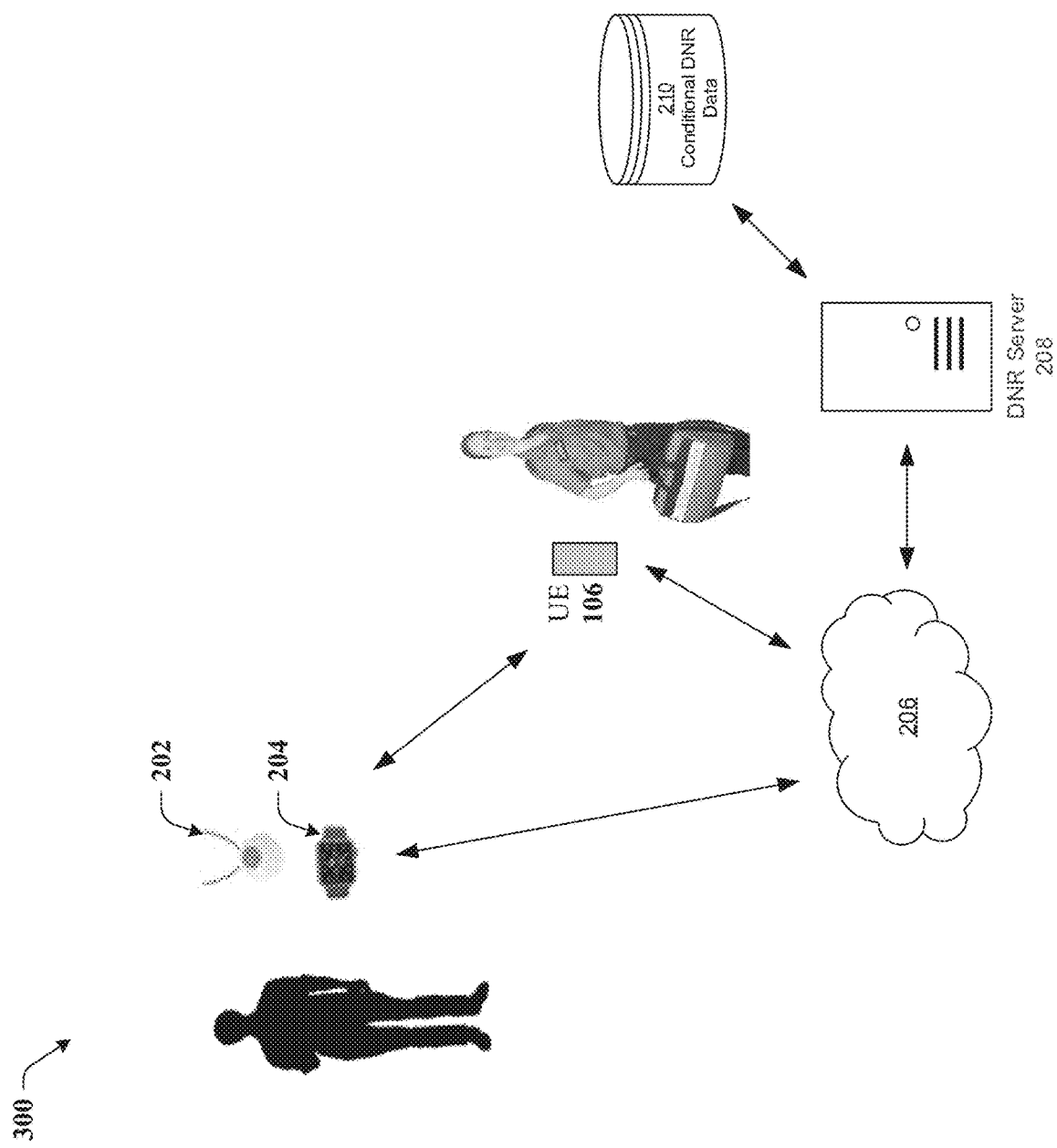
FIG. 3 illustrates an example schematic system block diagram of a DNR system according to one or more embodiments.
Figure 4:
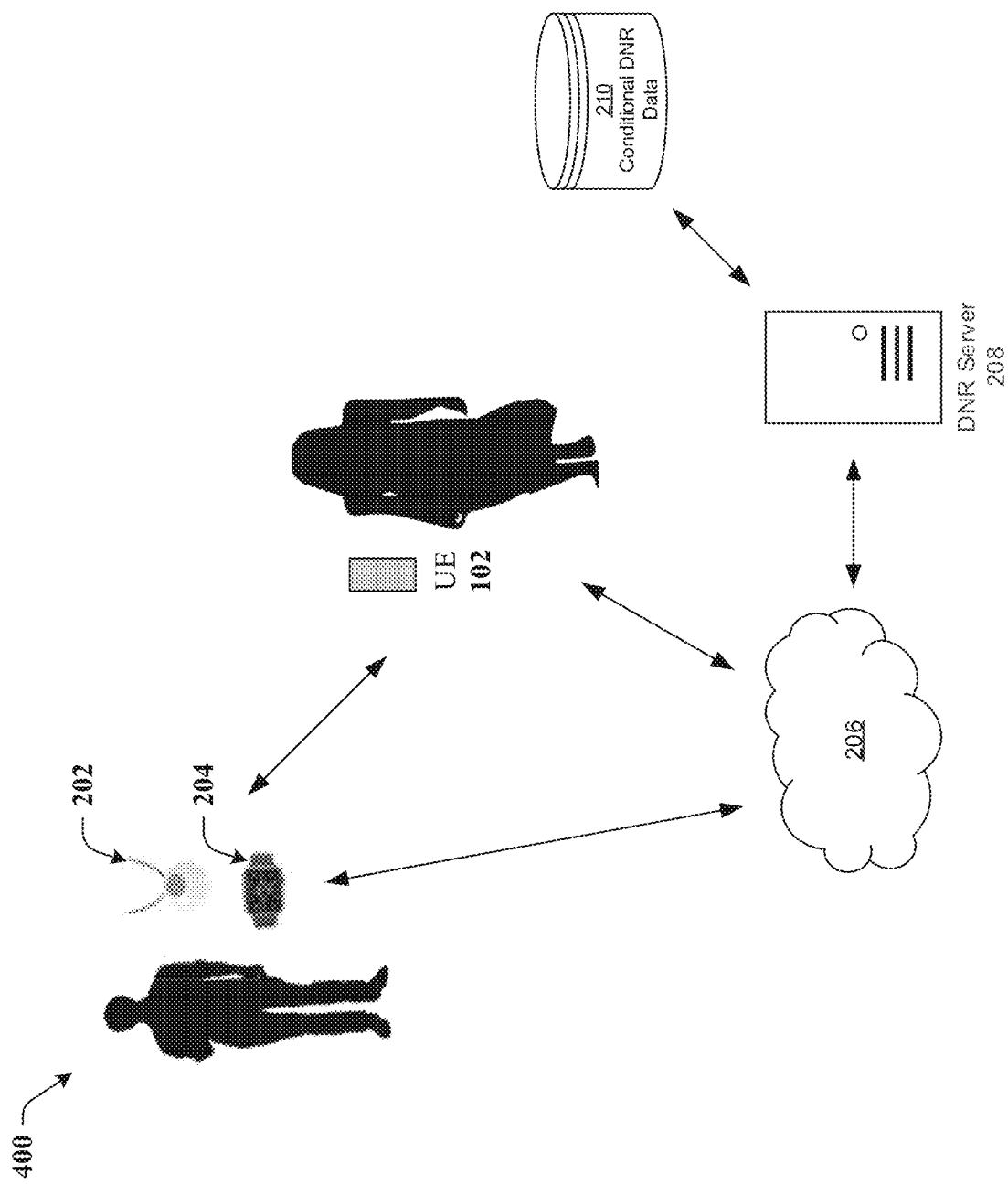
FIG. 4 illustrates an example schematic system block diagram of a DNR system according to one or more embodiments.

Referring now to FIG. 3 and FIG. 4, illustrated are example schematic system block diagram of a DNR system 300, 400 according to one or more embodiments.

As depicted in FIG. 3, in the case of a first responder, the instructions can be delivered to a communication device (e.g., UE 106) that they carry or wear. The first responder can proactively query using their device (e.g., UE 106) to determine if the person has conditional DNR on file. This can be necessary particularly if the person does not have their emergency pendant, smart watch, or other device 202, 204 with them.

With regards FIG. 4, in regards to the case of persons required to be present in order for a DNR to be executed, the conditional DNR app on the person's device 202, 204 can attempt to locate other devices (UE 102) in the immediate area using a near-field communication, such as Bluetooth. In doing so, the user's conditional DNR app can successfully sense or pair with the other device (UE 102), such as a family member's smartphone (UE 102). If a stored device ID (associated with the UE 102) is found via the DNR server 208, then the family member can be determined to be present and the instruction sent to the other device (UE 102) and/or the user's device 202, 204 can be: "do not resuscitate".

Figure 5:
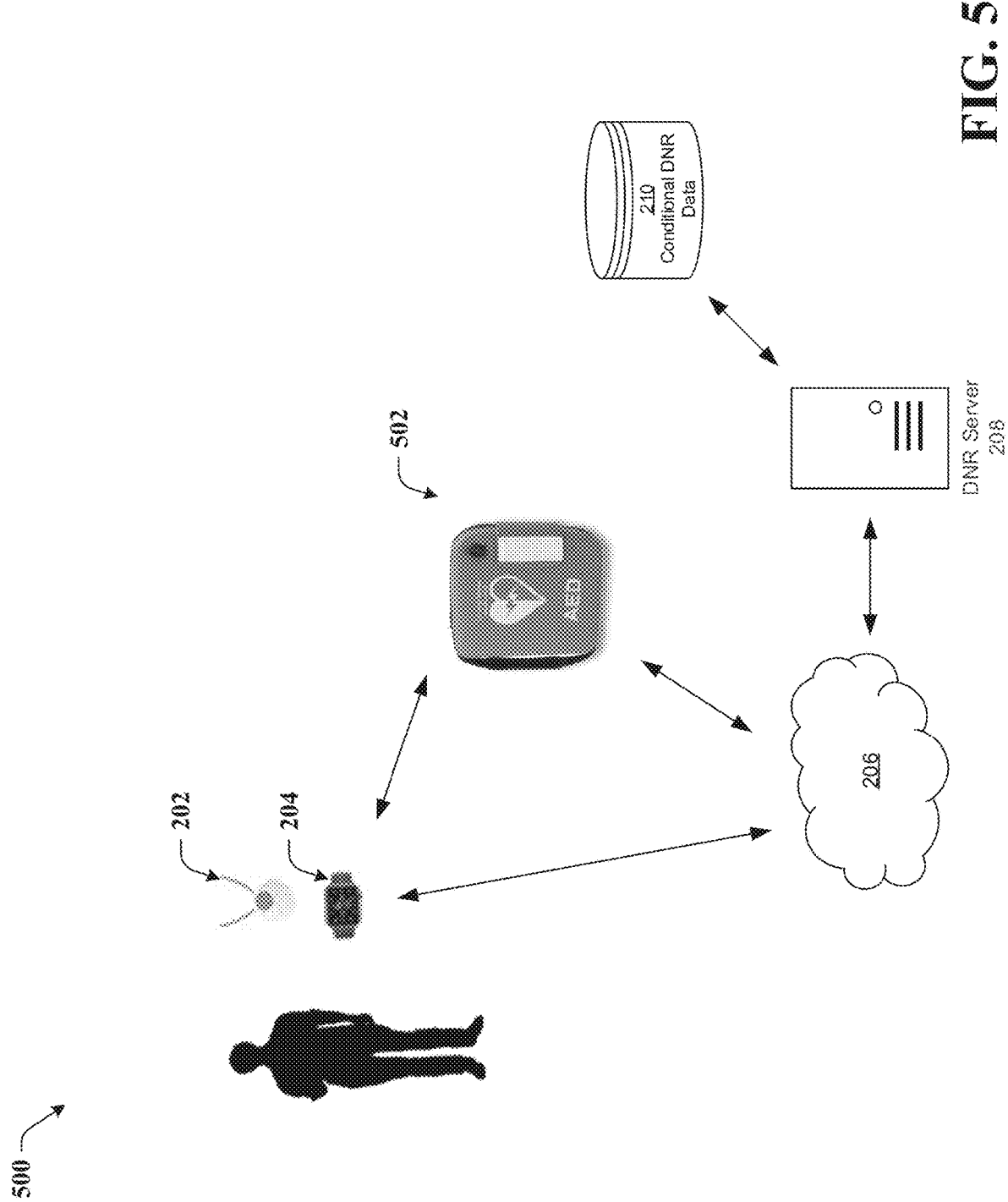
FIG. 5 illustrates an example schematic system block diagram of a DNR system comprising an automated external defibrillator according to one or more embodiments.

Referring now to FIG. 5 illustrates an example schematic system block diagram of a DNR system comprising an automated external defibrillator according to one or more embodiments.

In yet another embodiment, in response to a health event being determined to have occurred and/or in response to a request from the device 202, 204, and/or another device 102, 106, the DNR command instructions can be delivered by the DNR server 208 or the conditional DNR app to the AED device 502 or other similar medical device. The AED device 502 can use its speakers to deliver the DNR instructions to a first responder or other user of the AED device 502. For instance, if the AED device 502 has identified and/or paired to the device 202, 204, it can request time, duration, and/or termination data representative of a time to terminate the resuscitation from the DNR server 208. Furthermore, the instructions delivered to the AED device 502 can be used by the AED device 502 to disable the AED device 502, for a determined period of time, from delivering treatment to the person if the instruction is "do not resuscitate".

Figure 6:
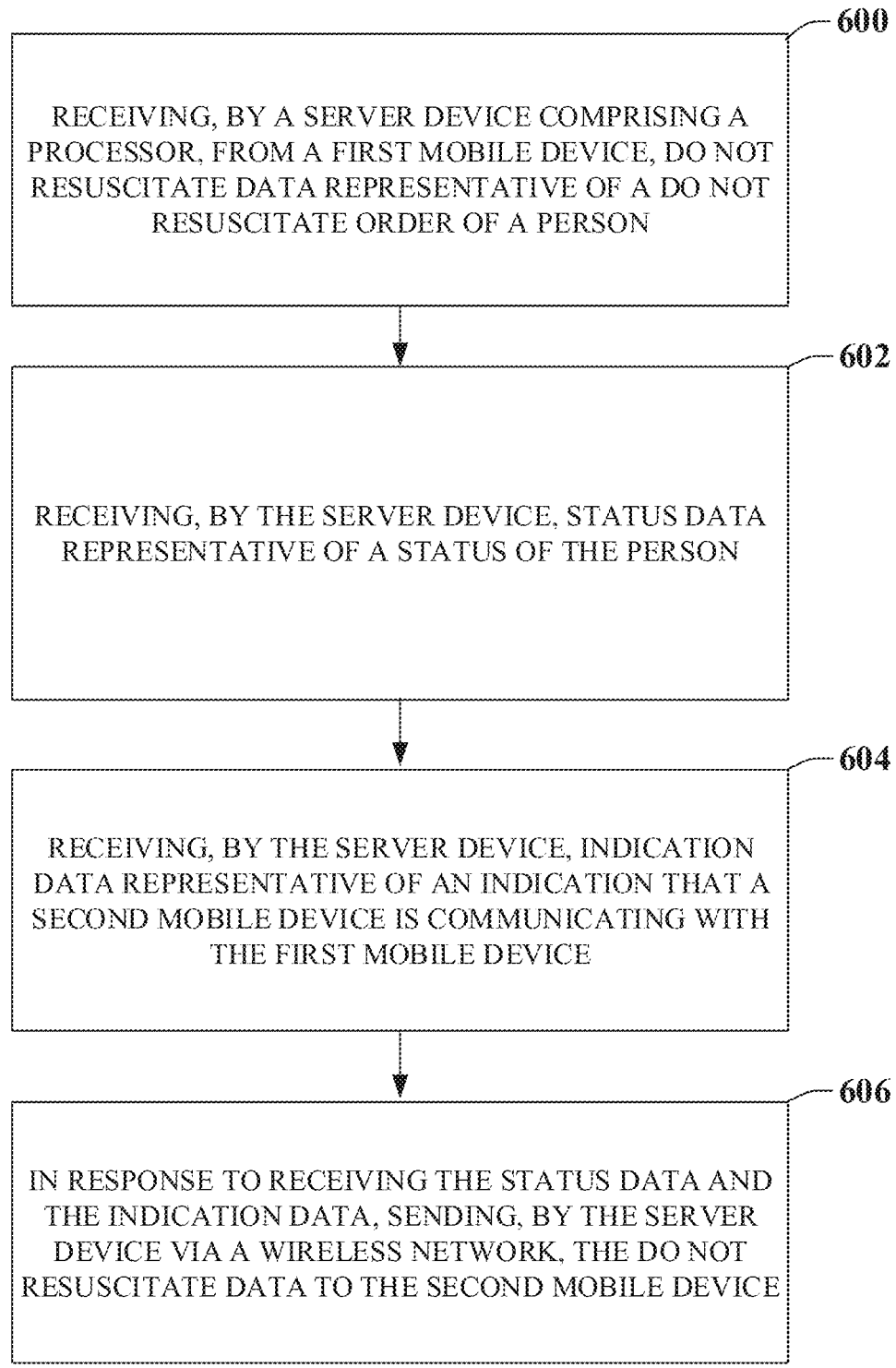
FIG. 6 illustrates an example flow diagram for a method for facilitating do not resuscitate orders according to one or more embodiments.
Figure 7:
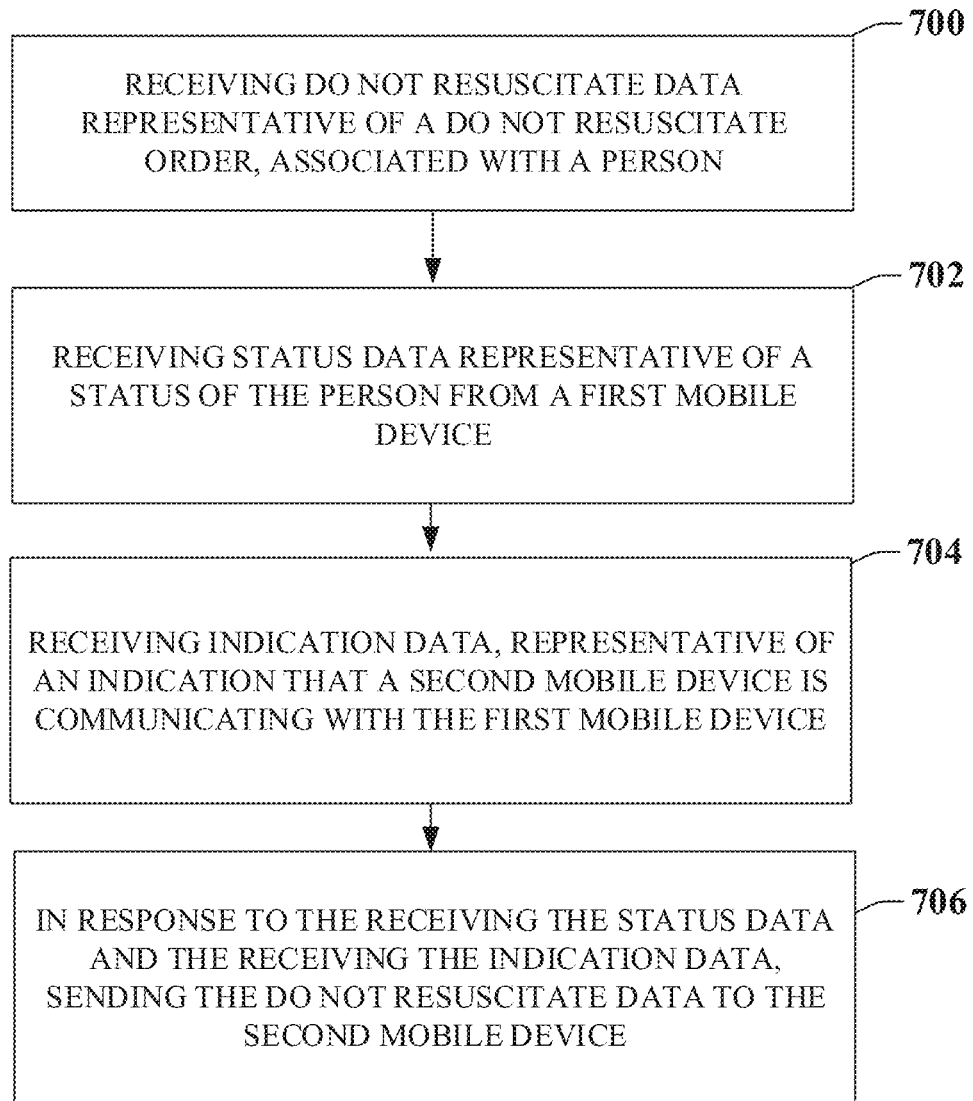
FIG. 7 illustrates an example flow diagram for a system for facilitating do not resuscitate orders according to one or more embodiments.

Referring now to FIG. 6, illustrated is an example flow diagram for a method for facilitating do not resuscitate orders according to one or more embodiments. At element 600, the method comprising receiving, by a server device comprising a processor, from a first mobile device, do not resuscitate data representative of a do not resuscitate order of a person. At element 602, the method can comprise receiving, by the server device, status data representative of a status of the person. Additionally, at element 604, the method can comprise receiving, by the server device, indication data representative of an indication that a second mobile device is communicating with the first mobile device. Furthermore, at element 606, in response to receiving the status data and the indication data, the method can comprise sending, by the server device via a wireless network, the do not resuscitate data to the second mobile device Referring now to FIG. 7, illustrated is an example flow diagram for a system for facilitating do not resuscitate orders according to one or more embodiments. At element 700, the system can facilitate receiving do not resuscitate data representative of a do not resuscitate order, associated with a person. At element 702, the system can comprise receiving status data representative of a status of the person from a first mobile device. Additionally, at element 704, the system can comprise receiving indication data, representative of an indication that a second mobile device is communicating with the first mobile device. Furthermore, in response to the receiving the status data and the receiving the indication data, at element 706, the system can comprise sending the do not resuscitate data to the second mobile device.

Figure 8:
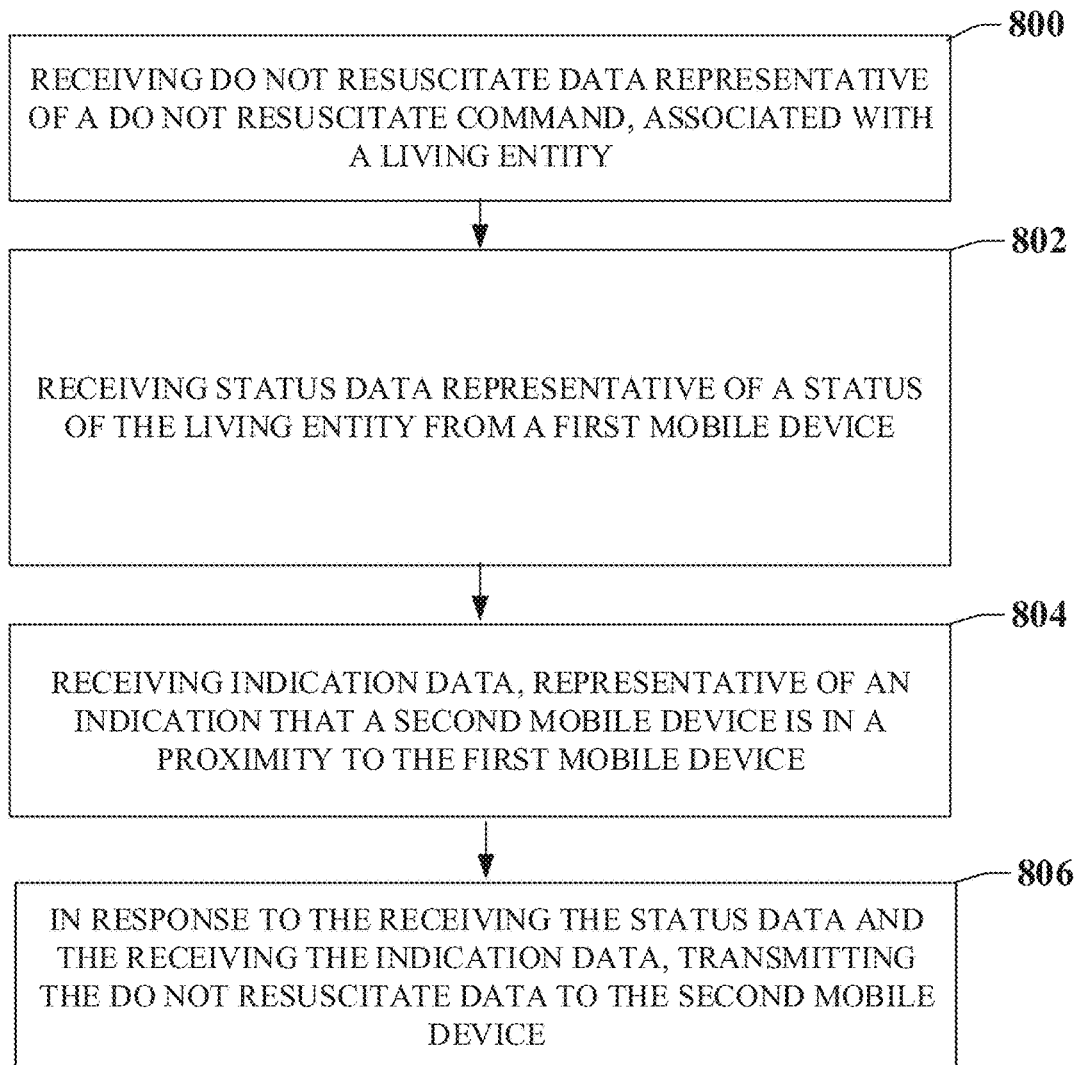
FIG. 8 illustrates an example flow diagram for a machine-readable medium for facilitating do not resuscitate orders according to one or more embodiments.

Referring now to FIG. 8, illustrated is an example flow diagram for a machine-readable medium for facilitating do not resuscitate orders according to one or more embodiments. At element 800, the machine-readable medium can perform the operations comprising receiving do not resuscitate data representative of a do not resuscitate command, associated with a living entity. At element 802, the machine-readable medium operations can comprise receiving status data representative of a status of the living entity from a first mobile device. At element 804, the machine-readable medium operations can comprise receiving indication data, representative of an indication that a second mobile device is in a proximity to the first mobile device. Additionally, at element 806, in response to the receiving the status data and the receiving the indication data, the machine-readable medium operations can comprise receiving transmitting the do not resuscitate data to the second mobile device.

Figure 9:
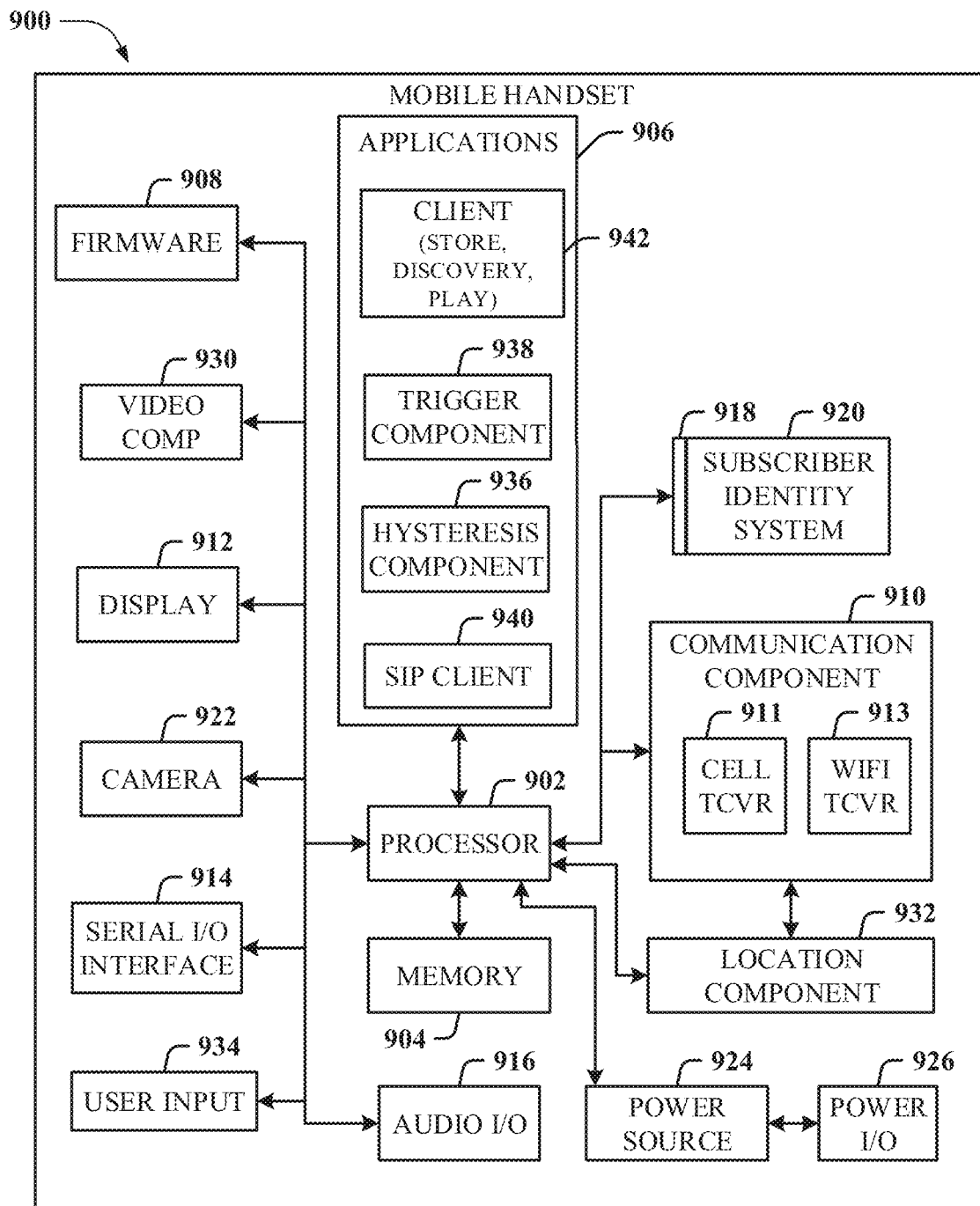
FIG. 9 illustrates an example block diagram of an example mobile handset operable to engage in a system architecture that facilitates secure wireless communication according to one or more embodiments described herein.

Referring now to FIG. 9, illustrated is a schematic block diagram of an exemplary end-user device such as a mobile device capable of connecting to a network in accordance with some embodiments described herein. Although a mobile handset 900 is illustrated herein, it will be understood that other devices can be a mobile device, and that the mobile handset 900 is merely illustrated to provide context for the embodiments of the various embodiments described herein. The following discussion is intended to provide a brief, general description of an example of a suitable environment 900 in which the various embodiments can be implemented. While the description includes a general context of computer-executable instructions embodied on a machine-readable storage medium, those skilled in the art will recognize that the innovation also can be implemented in combination with other program modules and/or as a combination of hardware and software.

Generally, applications (e.g., program modules) can include routines, programs, components, data structures, etc., that perform particular tasks or implement particular abstract data types. Moreover, those skilled in the art will appreciate that the methods described herein can be practiced with other system configurations, including single-processor or multiprocessor systems, minicomputers, mainframe computers, as well as personal computers, hand-held computing devices, microprocessor-based or programmable consumer electronics, and the like, each of which can be operatively coupled to one or more associated devices.

A computing device can typically include a variety of machine-readable media. Machine-readable media can be any available media that can be accessed by the computer and includes both volatile and non-volatile media, removable and non-removable media. By way of example and not limitation, computer-readable media can comprise computer storage media and communication media. Computer storage media can include volatile and/or non-volatile media, removable and/or non-removable media implemented in any method or technology for storage of information, such as computer-readable instructions, data structures, program modules or other data. Computer storage media can include, but is not limited to, RAM, ROM, EEPROM, flash memory or other memory technology, CD ROM, digital video disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

The handset 900 includes a processor 902 for controlling and processing all onboard operations and functions. A memory 904 interfaces to the processor 902 for storage of data and one or more applications 906 (e.g., a video player software, user feedback component software, etc.). Other applications can include voice recognition of predetermined voice commands that facilitate initiation of the user feedback signals. The applications 906 can be stored in the memory 904 and/or in a firmware 908, and executed by the processor 902 from either or both the memory 904 or/and the firmware 908. The firmware 908 can also store startup code for execution in initializing the handset 900. A communications component 910 interfaces to the processor 902 to facilitate wired/wireless communication with external systems, e.g., cellular networks, VoIP networks, and so on. Here, the communications component 910 can also include a suitable cellular transceiver 911 (e.g., a GSM transceiver) and/or an unlicensed transceiver 913 (e.g., Wi-Fi, WiMax) for corresponding signal communications. The handset 900 can be a device such as a cellular telephone, a PDA with mobile communications capabilities, and messaging-centric devices. The communications component 910 also facilitates communications reception from terrestrial radio networks (e.g., broadcast), digital satellite radio networks, and Internet-based radio services networks.

The handset 900 includes a display 912 for displaying text, images, video, telephony functions (e.g., a Caller ID function), setup functions, and for user input. For example, the display 912 can also be referred to as a "screen" that can accommodate the presentation of multimedia content (e.g., music metadata, messages, wallpaper, graphics, etc.). The display 912 can also display videos and can facilitate the generation, editing and sharing of video quotes. A serial I/O interface 914 is provided in communication with the processor 902 to facilitate wired and/or wireless serial communications (e.g., USB, and/or IEEE 1394) through a hardwire connection, and other serial input devices (e.g., a keyboard, keypad, and mouse). This supports updating and troubleshooting the handset 900, for example. Audio capabilities are provided with an audio I/O component 916, which can include a speaker for the output of audio signals related to, for example, indication that the user pressed the proper key or key combination to initiate the user feedback signal. The audio I/O component 916 also facilitates the input of audio signals through a microphone to record data and/or telephony voice data, and for inputting voice signals for telephone conversations. It should be noted that the microphone can be a digital or a non-digital microphone. For example, if the microphone is digital, it can produce audio data, however, the microphone can be non-digital and produce an audio signal that can be digitized by an analog-to-digital converter to produce the outputs for facilitation of the scenarios outlined in this disclosure.

The handset 900 can include a slot interface 918 for accommodating a SIC (Subscriber Identity Component) in the form factor of a card Subscriber Identity Module (SIM) or universal SIM 920, and interfacing the SIM card 920 with the processor 902. However, it is to be appreciated that the SIM card 920 can be manufactured into the handset 900, and updated by downloading data and software.

The handset 900 can process IP data traffic through the communication component 910 to accommodate IP traffic from an IP network such as, for example, the Internet, a corporate intranet, a home network, a person area network, etc., through an ISP or broadband cable provider. Thus, VoIP traffic can be utilized by the handset 900 and IP-based multimedia content can be received in either an encoded or decoded format.

A video processing component 922 (e.g., a camera) can be provided for decoding encoded multimedia content. The video processing component 922 can aid in facilitating the generation, editing and sharing of video quotes. The handset 900 also includes a power source 924 in the form of batteries and/or an AC power subsystem, which power source 924 can interface to an external power system or charging equipment (not shown) by a power I/O component 926.

The handset 900 can also include a video component 930 for processing video content received and, for recording and transmitting video content. For example, the video component 930 can facilitate the generation, editing and sharing of video quotes. A location tracking component 932 facilitates geographically locating the handset 900. As described hereinabove, this can occur when the user initiates the feedback signal automatically or manually. A user input component 934 facilitates the user initiating the quality feedback signal. The user input component 934 can also facilitate the generation, editing and sharing of video quotes. The user input component 934 can include such conventional input device technologies such as a keypad, keyboard, mouse, stylus pen, and/or touch screen, for example.

Referring again to the applications 906, a hysteresis component 936 facilitates the analysis and processing of hysteresis data, which is utilized to determine when to associate with the access point. A software trigger component 938 can be provided that facilitates triggering of the hysteresis component 938 when the Wi-Fi transceiver 913 detects the beacon of the access point. A SIP client 940 enables the handset 900 to support SIP protocols and register the subscriber with the SIP registrar server. The applications 906 can also include a client 942 that provides at least the capability of discovery, play and store of multimedia content, for example, music.

The handset 900, as indicated above related to the communications component 910, includes an indoor network radio transceiver 913 (e.g., Wi-Fi transceiver). This function supports the indoor radio link, such as IEEE 802.11, for the dual-mode GSM handset 900. The handset 900 can accommodate at least satellite radio services through a handset that can combine wireless voice and digital radio chipsets into a single handheld device.

Figure 10:
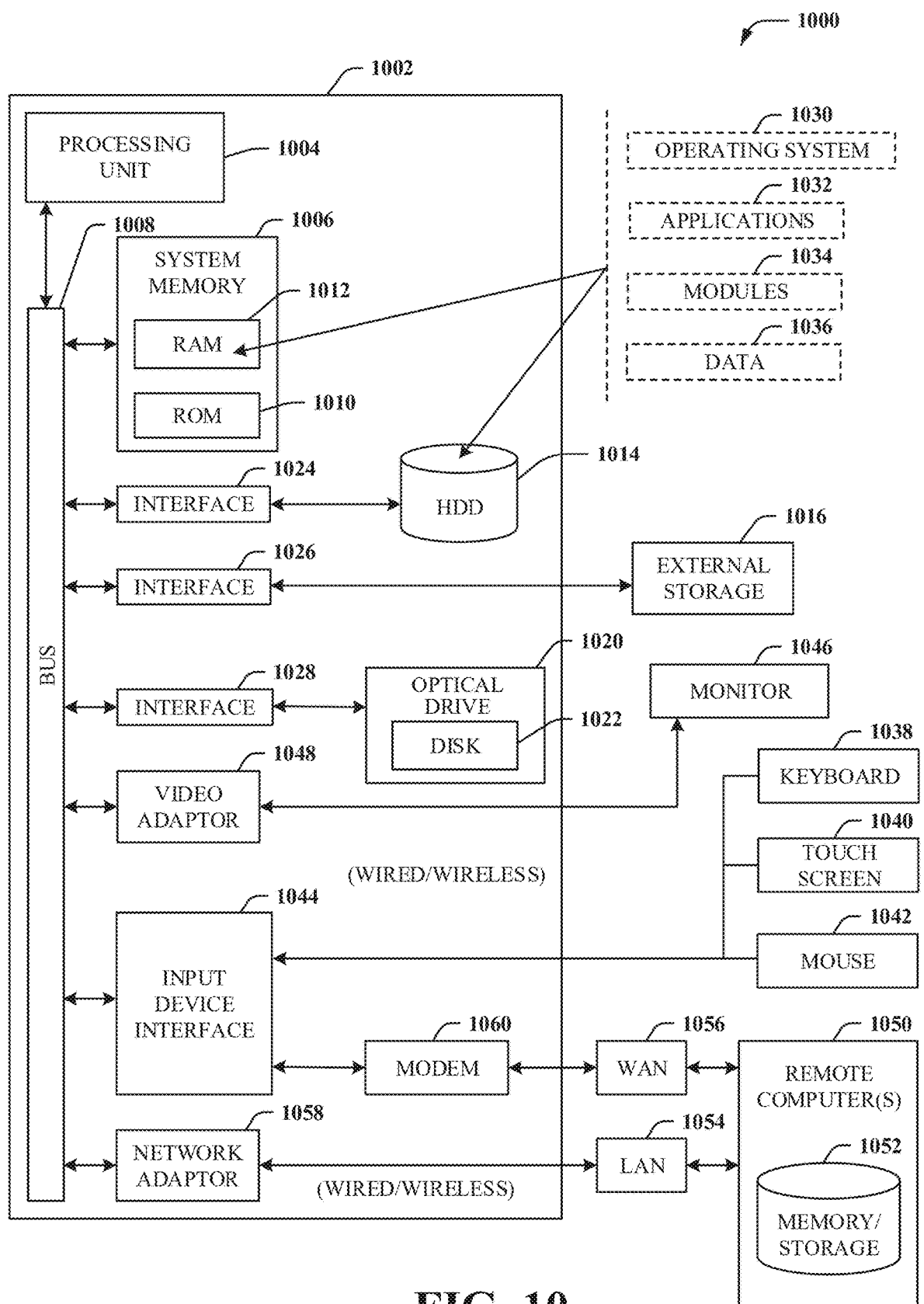
FIG. 10 illustrates an example block diagram of an example computer operable to engage in a system architecture that facilitates secure wireless communication according to one or more embodiments described herein.

In order to provide additional context for various embodiments described herein, FIG. 10 and the following discussion are intended to provide a brief, general description of a suitable computing environment 1000 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the disclosed methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 10, the example environment 1000 for implementing various embodiments of the aspects described herein includes a computer 1002, the computer 1002 including a processing unit 1004, a system memory 1006 and a system bus 1008. The system bus 1008 couples system components including, but not limited to, the system memory 1006 to the processing unit 1004. The processing unit 1004 can be any of various commercially available processors. Dual microprocessors and other multi-processor architectures can also be employed as the processing unit 1004.

The system bus 1008 can be any of several types of bus structure that can further interconnect to a memory bus (with or without a memory controller), a peripheral bus, and a local bus using any of a variety of commercially available bus architectures. The system memory 1006 includes ROM 1010 and RAM 1012. A basic input/output system (BIOS) can be stored in a non-volatile memory such as ROM, erasable programmable read only memory (EPROM), EEPROM, which BIOS contains the basic routines that help to transfer information between elements within the computer 1002, such as during startup. The RAM 1012 can also include a high-speed RAM such as static RAM for caching data.

The computer 1002 further includes an internal hard disk drive (HDD) 1014 (e.g., EIDE, SATA), one or more external storage devices 1016 (e.g., a magnetic floppy disk drive (FDD) 1016, a memory stick or flash drive reader, a memory card reader, etc.) and an optical disk drive 1020 (e.g., which can read or write from a CD-ROM disc, a DVD, a BD, etc.). While the internal HDD 1014 is illustrated as located within the computer 1002, the internal HDD 1014 can also be configured for external use in a suitable chassis (not shown). Additionally, while not shown in environment 1000, a solid state drive (SSD) could be used in addition to, or in place of, an HDD 1014. The HDD 1014, external storage device(s)

1016 and optical disk drive 1020 can be connected to the system bus 1008 by an HDD interface 1024, an external storage interface 1026 and an optical drive interface 1028, respectively. The interface 1024 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1002, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1012, including an operating system 1030, one or more application programs 1032, other program modules 1034 and program data 1036. All or portions of the operating system, applications, modules, and/or data can also be cached in the RAM 1012. The systems and methods described herein can be implemented utilizing various commercially available operating systems or combinations of operating systems.

Computer 1002 can optionally comprise emulation technologies. For example, a hypervisor (not shown) or other intermediary can emulate a hardware environment for operating system 1030, and the emulated hardware can optionally be different from the hardware illustrated in FIG. 10. In such an embodiment, operating system 1030 can comprise one virtual machine (VM) of multiple VMs hosted at computer 1002. Furthermore, operating system 1030 can provide runtime environments, such as the Java runtime environment or the .NET framework, for applications 1032. Runtime environments are consistent execution environments that allow applications 1032 to run on any operating system that includes the runtime environment. Similarly, operating system 1030 can support containers, and applications 1032 can be in the form of containers, which are lightweight, standalone, executable packages of software that include, e.g., code, runtime, system tools, system libraries and settings for an application.

Further, computer 1002 can be enable with a security module, such as a trusted processing module (TPM). For instance with a TPM, boot components hash next in time boot components, and wait for a match of results to secured values, before loading a next boot component. This process can take place at any layer in the code execution stack of computer 1002, e.g., applied at the application execution level or at the operating system (OS) kernel level, thereby enabling security at any level of code execution.

A user can enter commands and information into the computer 1002 through one or more wired/wireless input devices, e.g., a keyboard 1038, a touch screen 1040, and a pointing device, such as a mouse 1042. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1004 through an input device interface 1044 that can be coupled to the system bus 1008, but can be connected by other interfaces, such as a parallel port, an IEEE 1394 serial port, a game port, a USB port, an IR interface, a BLUETOOTH® interface, etc.

A monitor 1046 or other type of display device can be also connected to the system bus 1008 via an interface, such as a video adapter 1048. In addition to the monitor 1046, a computer typically includes other peripheral output devices (not shown), such as speakers, printers, etc.

The computer 1002 can operate in a networked environment using logical connections via wired and/or wireless communications to one or more remote computers, such as a remote computer(s) 1050. The remote computer(s) 1050 can be a workstation, a server computer, a router, a personal computer, portable computer, microprocessor-based entertainment appliance, a peer device or other common network node, and typically includes many or all of the elements described relative to the computer 1002, although, for purposes of brevity, only a memory/storage device 1052 is illustrated. The logical connections depicted include wired/wireless connectivity to a local area network (LAN) 1054 and/or larger networks, e.g., a wide area network (WAN) 1056. Such LAN and WAN networking environments are commonplace in offices and companies, and facilitate enterprise-wide computer networks, such as intranets, all of which can connect to a global communications network, e.g., the Internet.

When used in a LAN networking environment, the computer 1002 can be connected to the local network 1054 through a wired and/or wireless communication network interface or adapter 1058. The adapter 1058 can facilitate wired or wireless communication to the LAN 1054, which can also include a wireless access point (AP) disposed thereon for communicating with the adapter 1058 in a wireless mode.

When used in a WAN networking environment, the computer 1002 can include a modem 1060 or can be connected to a communications server on the WAN 1056 via other means for establishing communications over the WAN 1056, such as by way of the Internet. The modem 1060, which can be internal or external and a wired or wireless device, can be connected to the system bus 1008 via the input device interface 1044. In a networked environment, program modules depicted relative to the computer 1002 or portions thereof, can be stored in the remote memory/storage device 1052. It will be appreciated that the network connections shown are example and other means of establishing a communications link between the computers can be used.

When used in either a LAN or WAN networking environment, the computer 1002 can access cloud storage systems or other network-based storage systems in addition to, or in place of, external storage devices 1016 as described above. Generally, a connection between the computer 1002 and a cloud storage system can be established over a LAN 1054 or WAN 1056 e.g., by the adapter 1058 or modem 1060, respectively. Upon connecting the computer 1002 to an associated cloud storage system, the external storage interface 1026 can, with the aid of the adapter 1058 and/or modem 1060, manage storage provided by the cloud storage system as it would other types of external storage. For instance, the external storage interface 1026 can be configured to provide access to cloud storage sources as if those sources were physically connected to the computer 1002.

The computer 1002 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

The computer is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10 BaseT wired Ethernet networks used in many offices.

The above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In this regard, while the subject matter has been described herein in connection with various embodiments and corresponding FIGs, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

What is claimed is:

1. A method, comprising:
  receiving, by a server device comprising a processor, from a first mobile device, do not resuscitate data representative of conditions that determine execution of a do not resuscitate order of a person;
  receiving, by the server device, status data representative of a status of the person;
  receiving, by the server device, indication data representative of an indication that a second mobile device is communicating with the first mobile device;
  in response to determining that a combination of the status data and the indication data do not satisfy the conditions, sending, by the server device via a wireless network, an attempt to resuscitate instruction for presentation via the second mobile device; and
  in response to determining that the combination of the status data and the indication data satisfy the conditions, sending, by the server device via the wireless network, a do not resuscitate instruction for presentation by the second mobile device.

2. The method of claim 1, wherein the conditions comprises threshold data representative of a threshold associated with the status of the person that is threshold satisfied in order to execute the do not resuscitate order.

3. The method of claim 2, wherein the status data comprises brain damage data representative of a brain damage of the person, and the threshold is a defined amount of brain damage.

4. The method of claim 2, wherein the conditions comprises a specified person that is to be present in order to execute the do not resuscitate order.

5. The method of claim 4, wherein the person is a first person, and wherein the indication data is further representative of a second person associated with the second mobile device.

6. The method of claim 1, wherein the status data comprises location data representative of a location of the person.

7. The method of claim 6, wherein a condition of the conditions is a function of the location of the person.

8. A system, comprising:
  a processor; and
  a memory that stores executable instructions that, when executed by the processor, facilitate performance of operations, comprising:
    receiving do not resuscitate data representative of a condition that determines implementation of a do not resuscitate order associated with a person;
    receiving status data representative of a status of the person from a first mobile device;
    receiving indication data, representative of an indication that a second mobile device is communicating with the first mobile device;
    in response to determining that a combination of the status data and the indication data do not satisfy the condition, sending a first command to the second mobile device to render a first instruction to attempt to resuscitate the person; and
    in response to the determining that the combination of the status data and the indication data satisfy the condition, sending a second command to the second mobile device to present a second instruction not to attempt to resuscitate the person.

9. The system of claim 8, wherein the do not resuscitate data comprises location data representative of a location.

10. The system of claim 9, wherein the condition is a function of the location when the person is determined to be at the location.

11. The system of claim 8, wherein the person is a first person, and wherein the do not resuscitate data comprises second person data representative of a second person.

12. The system of claim 11, wherein the condition is a function of the second person having been determined to be in a defined proximity of the first person.

13. The system of claim 8, wherein the operations further comprise: in further response to the determining that the combination of the status data and the indication data satisfy the condition, determining, from the condition, a time at which the do not resuscitate order is to be executed.

14. The system of claim 8, wherein the operations further comprise: in further response to the determining that the combination of the status data and the indication data do not satisfy the condition, determining, from the condition, a date on which the do not resuscitate order is not to be executed.

15. A non-transitory machine-readable medium, comprising executable instructions that, when executed by a processor, facilitate performance of operations, comprising:
receiving do not resuscitate data representative of conditions that determine initiation of a do not resuscitate command associated with a living entity;
receiving status data representative of a status of the living entity from a first mobile device;
receiving indication data, representative of an indication that a second mobile device is in a proximity to the first mobile device;
in response to determining that a combination of the status data and the indication data do not satisfy the conditions, sending an attempt to resuscitate command for presentation via a user interface of the second mobile device; and
in response to determining that the combination of the status data and the indication data satisfy the conditions, transmitting the do not resuscitate command for presentation via the user interface of the second mobile device.

16. The non-transitory machine-readable medium of claim 15, wherein the second mobile device is associated with an emergency medical response entity.

17. The non-transitory machine-readable medium of claim 15, wherein the do not resuscitate command comprises time data representative of a time period during which the do not resuscitate command is to be executed.

18. The non-transitory machine-readable medium of claim 17, wherein the operations further comprise:
transmitting the time data to a defibrillator device to be used to control resuscitation of the living entity at least in part using the defibrillator device.

19. The non-transitory machine-readable medium of claim 18, wherein the operations further comprise:
in response to the time period being determined to have expired, transmitting a disable command directed to the defibrillator device to disable the defibrillator device from control of the resuscitation of the living entity.

20. The non-transitory machine-readable medium of claim 15, wherein the status data comprises function data representative of a function of an organ of the living entity.

* * * * *